(12) United States Patent
Leeper et al.

(10) Patent No.: US 8,188,006 B2
(45) Date of Patent: *May 29, 2012

(54) SYNERGISTIC COMPOSITION AND METHOD OF USE

(75) Inventors: John R. Leeper, Las Cruces, NM (US); Craig A. Sandoski, Collierville, TN (US)

(73) Assignee: Riceco, LLC, Memphis, TN (US)

( * ) Notice: Subject to any disclaimer, the term of this patent is extended or adjusted under 35 U.S.C. 154(b) by 55 days.

This patent is subject to a terminal disclaimer.

(21) Appl. No.: 12/869,944

(22) Filed: Aug. 27, 2010

(65) Prior Publication Data

US 2011/0053774 A1    Mar. 3, 2011

Related U.S. Application Data

(60) Provisional application No. 61/237,786, filed on Aug. 28, 2009, provisional application No. 61/354,769, filed on Jun. 15, 2010.

(51) Int. Cl.
*A01N 43/40* (2006.01)
(52) U.S. Cl. ..................................... 504/130
(58) Field of Classification Search ........................ None
See application file for complete search history.

(56) References Cited

U.S. PATENT DOCUMENTS

| | | | |
|---|---|---|---|
| 5,905,060 A | 5/1999 | Fenderson et al. | |
| 2003/0203819 A1 | 10/2003 | Sievernich | |
| 2011/0098182 A1* | 4/2011 | Mann et al. | 504/136 |

FOREIGN PATENT DOCUMENTS

WO     WO 2004-008861 A1     1/2004

OTHER PUBLICATIONS

Norsworthy, J.K., "Herbicide options for rice cutgrass (*Leersia oryzoides*) control", Weed Technology, Mar. 2009, vol. 23, pp. 1-5.
Norsworthy, J.K. et al., "Consultant perspectives on week management needs in Arkansas rice", Weed Technology, 2007, vol. 21, pp. 832-839.
PCT international search report and the written opinion of the international searchrig authority or the declaration, May 23, 2011.

* cited by examiner

*Primary Examiner* — Alton Pryor
(74) *Attorney, Agent, or Firm* — Harris, Shelton Hannover & Walsh

(57) ABSTRACT

The present invention relates to a method to increase the effectiveness of an imidazolinone herbicide to suppress weedy forms of rice growth used with imidazolinone tolerant rice strains. This method involves applying an imidazolinone herbicide to imidazolinone tolerant rice strains in a field and applying either a propanil based herbicide or a thiobencarb herbicide to this rice crop, wherein the herbicide includes a synergistically effective amount a herbicidally inactive ingredient. The propanil based herbicide synergistically affects the activity of an imidazolinone herbicide by increasing the effectiveness of an imidazolinone herbicide used with the rice to suppress weedy forms of rice growth, such as red rice.

14 Claims, 8 Drawing Sheets

SYNERGISTIC COMPOSITION AND METHOD OF USE

RELATED APPLICATION

This application is a continuation of a U.S. Ser. 61/237,786 filed, Aug. 28, 2009 and a continuation of U.S. Ser. No. 61,354,769, filed Jun. 15, 2010 and hereby claims the benefit under 35 U.S.C. Sec. 119(e) thereof and specifically incorporates these patent applications by reference.

FIELD OF THE INVENTION

This invention relates to a method to use synergistic combinations, particularly, such combinations for use in controlling weeds in imidazolinone tolerant rice strains.

BACKGROUND OF THE INVENTION

Imidazolinone herbicides are used in a wide range of crops where the crop is tolerant of the imidazolinone and weeds in the crop are susceptible. There are also cases where weeds have become resistant to the imidazolinone herbicides. Rice is naturally susceptible to imidazolinone herbicides. However, resistance was developed within a line of rice that led to commercialization of conventional and hybrid rice varieties currently sold as CLEARFIELD (BASF) rice. NEWPATH (imazethapyr) (BASF) can be sprayed on CLEARFIELD (BASF) rice without injury to the plants. This has become a leading method for controlling weedy forms of rice, a weedy forms or rice that is not tolerant of imidazolinone herbicides, in a crop of rice that is tolerant to the imidazolinone herbicide. The imidazolinone sprayed on to CLEARFIELD (BASF) rice also controls other weeds, particularly barnyard grass. NEWPATH (imazethapyr) (BASF) is typically applied at the two- to three-leaf and at the 3-4 leaf stage of weedy forms of rice, such as red rice.

A number of problems, however, have developed with the use of the imidazolinones on CLEARFIELD (BASF) rice. They include: some grass weeds have developed resistance to the imidazolinones and are no longer adequately controlled with the use of the imidazolinones; out crossing of the imidazolinone resistant gene into weedy forms of rice is occurring, making the weedy forms of rice less susceptible to the imidazolinone herbicides; and a portion of the CLEARFIELD (BASF) rice F1 crop is dropped into the field at harvest or due to other factors and can become weedy rice forms with partial tolerance to the imidazolinones in future seasons. Additionally, as the herbicides are sprayed via airplanes some areas of the field may receive less than required amounts of the imidazolinone.

SUMMARY OF THE INVENTION

The present invention relates a method to increase the effectiveness of an imidazolinone herbicide to suppress weedy forms of rice growth used with imidazolinone tolerant rice strains. This method includes the steps of applying an imidazolinone herbicide to imidazolinone tolerant rice and applying a propanil based herbicide to this rice, wherein the propanil based herbicide includes a herbicidally effective amount a herbicidally active ingredient including propanil and a synergistically effective amount a herbicidally inactive ingredient to synergistically affect the activity of a imidazolinone herbicide to increase the effectiveness of an imidazolinone herbicide to suppress undesirable weedy forms of rice growth, such as red rice.

The present invention relates to the use of emulsifiers, adjuvant, crop protection chemicals that when applied in combination with the imidazolinone herbicide potentiates or synergizes the imidazolinones herbicidal activity in controlling susceptible and resistant weeds including weedy forms of rice, weedy forms of rice with partial imidazolinone tolerance due to out crossing, and F1 rice that does not possess full tolerance to the imidazolinones.

BRIEF DESCRIPTION OF DRAWINGS

FIG. 5 shows Red Rice control (%) with NEWPATH and NEWPATH+RICEBEAUX evaluated at 22 Days after EPOST and 9 Days after LPOST. Means followed by the same letter do not significantly differ (P=0.05). Legend: EPOST: early post emergence, LPOST: late postemergence, and fb: followed by.

DETAILED DESCRIPTION OF THE INVENTION

Figure 1:
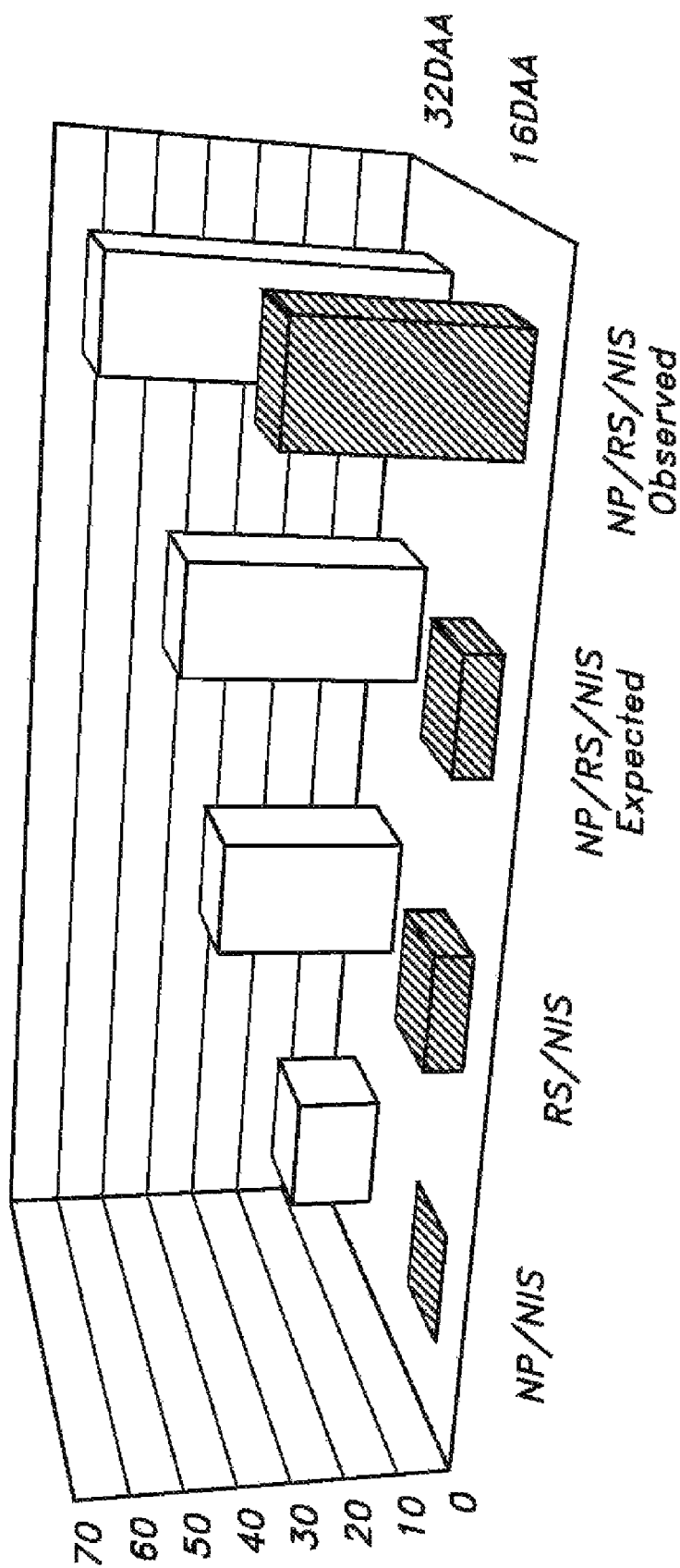
FIG. 1 shows expected versus observed Red Rice control (%) with NEWPATH and (1 oz./A.) and RICESHOT (2.25 qt./A.) with NIS (0.25% v/v) at 16 and 32 DAA. Expected values are based on Colby Method (Weeds 15:20-22). Legend: NP: NEWPATH, NIS: Non-ionic Surfactant and, RS: RICESHOT.

This invention relates to a method to use synergistic combinations, particularly, such combinations for use in controlling weeds in imidazolinone tolerant rice strains, such as CLEARFIELD (BASF) rice crops. Imidazolinone herbicides are used in a wide range of crops where the crop is tolerant of the imidazolinone and weeds in the crop are susceptible. For example, imidazolinone is used to control weedy forms of rice while cultivating imidazolinone tolerant rice strains rice crops.

This method includes the steps of applying an imidazolinone herbicide to imidazolinone tolerant rice and applying a propanil based herbicide to this rice, wherein the propanil based herbicide includes a herbicidally effective amount a herbicidally active ingredient including propanil. Other herbicidally effective herbicides can be added to the propanil based herbicide, such as thiobencarb and quinclorac. The term "propanil based herbicide' means that propanil is a required active ingredient in the herbicide. For example, thiobencarb can be mixed or co applied with the propanil based herbicide to synergistically affect the activity of an imidazolinone herbicide. The term "synergistic" means an inhibition or control of weed growth by a combination of chemicals that is greater than would be expected if the chemicals were used individually. This term "synergistic" as used herein is based on formula II from Colby, Calculating Synergistic and Antagonistic Responses of Herbicidal Combinations, 15 Weeds 20 (1967) (hereby specifically incorporated by reference in its entirety). At least 7.0% increase in control of weedy forms of rice was observed based on Colby's formula.

It has been surprisingly found that non-herbicidally active compounds synergistically affect the activity of an imidazolinone herbicide by increasing the effectiveness of an imidazolinone herbicide to suppress weedy forms of rice growth. These herbicidally in-active ingredients include adjuvants that have synergistic effects on imidazolinone herbicide used on imidazolinone tolerant rice strain. In particular, the synergistic effect is such that beneficial effect can be observed after only one application of an imidazolinone herbicide.

An adjuvant is something which is added to a spray solution to increase the effectiveness of the active ingredient. An adjuvant may be packaged and formulated with the herbicide product or they may be added to the spray solution as a tank mix. Surfactants are adjuvants used to increase the dispersing, spreading, wetting, or other properties of the liquids. This term is derived from the words surface active agent. Surfactant molecules are made of two parts: a strong polar group that is attracted to water and a non-polar group attracted to non-aqueous materials, such as oil. Of the types of surfactants, the nonionic surfactants are the most common in agricultural sprays. A crop oil is an emulsifiable petroleum oil-based product that may contain up to 5 percent surfactants with the remainder being a phytobland oil. A crop oil concentrate (COC) is made of a non-phototoxic (not causing injury) mineral and/or vegetable oil. A crop oil concentrate contains up to twenty percent surfactant. The principal function of these materials is to aid in moving the herbicide across the leaf cuticle and reduce the surface tension of the spray droplets. Crop oils are also effective at increasing spray retention on leaf surfaces and reducing drying times. This allows more time for the herbicide to penetrate the leaf.

The inactive portion of the adjuvant can also include an effective amount of nonpolar aromatic hydrocarbon adjuvant (e.g. isophorone, mesitylene oxide and xylene in the finished product formulation) in combination with imidazolinone herbicides that potentiates or synergizes the imidazolinone herbicide activity in controlling susceptible and tolerant weeds including weedy forms of rice, weedy forms of rice, with partial imidazolinone tolerance due to out crossing, and F1 CLEARFIELD (BASF) rice that does not possess full tolerance to the imidazolinones.

An herbicidal formulation, according to the invention, includes directly sprayable aqueous solutions, suspensions concentrate (SC), highly-concentrated aqueous, oily or other suspensions or dispersions, emulsions, oil dispersions, pastes, materials for spreading, which can be applied by means of spraying, atomizing, spreading or pouring. Emulsifiable concentrate (EC) formulations conventionally contain an active ingredient, one or more surfactants which act as emulsifiers upon dilution of the EC with water and a water immiscible solvent. Typical solvents for conventional EC formulations are aromatic hydrocarbons. These solvents have very low solubility in water and a high capability of dissolving a wide range of active ingredients.

Additional suitable inert additives (auxiliaries), for example mineral oil fractions of medium to high boiling point such as kerosene and diesel oil, furthermore coal tar oils and oils of vegetable or animal origin, aliphatic, cyclic and aromatic hydrocarbons, e.g. paraffins, tetrahydronaphthalene, alkylated naphthalenes and their derivatives, alkylated benzenes and their derivatives, alcohols such as methanol, ethanol, propanol, butanol and cyclohexanol, ketones such as cyclohexanone, strongly polar solvents, such as N-methylpyrrolidone.

Additionally, imidazolinone herbicides can also be synergized by adjuvants used as spray tank additives (crop oil concentrates, non-ionic surfactants, spreader stickers). These combinations produce synergistic or unexpected control of weeds in rice when applied at various times, and to rice planted in different ways. To control the weeds, the combination may be applied prior to planting, after planting but prior to flooding (pre-flood, post-emergence) or after emergence of the rice and flooding (post-flood, post-emergence) and may be applied to either direct seeded (drilled or surface seeded) or transplanted rice.

To be used in combination, it is not necessary that the imidazolinone and the synergistically active chemical or chemicals be applied in a physically combined form, or even at the same time. The combination effect results so long as the imidazolinone and the synergistically active chemical or chemicals are present in or on the targeted foliage of the weeds at the same time in the rice crop, regardless of when they were applied.

Either the imidazolinone and the synergistically active chemical or chemicals could thus be applied in liquid or solid form, or a combination product containing both the Imidazolinone and the synergistically active chemical or chemicals could be produced, again, in either liquid or solid form. Typical liquid formulations include emulsions, suspensions (including suspensions containing microcapsules), solutions, emulsifiable concentrates, and flowables. Solid products include forms such as granules, wettable powders, water-dispersible solid products (including water-dispersible granules containing microencapsulated pesticides) or dusts. Both types of compositions will generally contain, in addition to the active herbicides other ingredients such as solvents, wetting agents, suspending agents, anti-caking agents, dispersing agents, emulsifiers, antifreeze agents, antifoam agents, and other additives.

Either the imidazolinone and the synergistically active chemical or chemicals, or both, may be utilized in one of a number of known forms of controlled release compositions. Such compositions provide relatively slow or controlled release of the active ingredient into the environment and include, for example, encapsulations, micro encapsulations, and various forms of controlled release liquid or granules.

Compositions according to this invention may contain the imidazolinone and the synergistically active chemical or chemicals in numerous different physical forms. In some cases, a composition may be produced by simply physically mixing ("tank mixing") commercially available products containing the active ingredients, for example, two emulsifiable concentrates containing the imidazolinone and the synergistically active chemical or chemicals. Alternatively, a package may be manufactured and sold which contains overall the Imidazolinone and the synergistically active chemical or chemicals in separate containers, but packaged together, commonly termed a "twin-pack".

Alternatively, previously prepared compositions ("premixes") containing the Imidazolinone and the synergistically active chemical or chemicals can be produced. Typical liquid compositions would include an emulsifiable concentrate containing both herbicides, and a two-phase emulsion (or micro emulsion) with one herbicide in each phase.

However, a similar solid product containing the imidazolinone and the synergistically active chemical or chemicals could likewise be produced, for instance, as impregnated granules. Similarly, other solid formulations such as wettable powders or dusts could be prepared.

Again similarly, using appropriate ingredients and conditions, it would be possible to prepare microencapsulated products in which one or both the imidazolinone and the synergistically active chemical or chemicals are contained within a microcapsule and said microencapsulated products could be sold in either liquid form (i.e., capsule suspensions) or solid form (i.e., water-dispersible granules produced by drying of microcapsule suspensions). One type of liquid form would be a microcapsule suspension in which one of the imidazolinone or the synergistically active chemical or chemicals is contained within the capsules while the other is present in a nonencapsulated form, in the continuous liquid phase. The types of formulations or compositions which may contain the imidazolinone and the synergistically active chemical or chemicals is not limited by those enumerated herein, as other types of formulations would likely be envisaged by those skilled in the art.

Additionally, other biocidically active ingredients or compositions may be combined with the herbicidal compositions of the present invention and used in the methods of the present invention. In addition, the synergistic active ingredients of the present invention can also include insecticides, fungicides, bactericides, acaracides, nematicides, plant growth regulators, fertilizers and plant nutrients, or other herbicides, especially herbicides known to be useful for controlling weeds in a rice crop.

These combinations produced synergistic control of weeds in rice when applied at various times, and to rice planted in different ways. To control the weeds, the synergistic composition may be applied prior to planting, after planting but prior to flooding (pre-flood, post-emergence) or after emergence of the rice and flooding (post-flood, post-emergence) and may be applied to either direct seeded (drilled or surface seeded) or transplanted rice.

The control of weedy forms of rice weeds by the combination of herbicidal composition including an effective amount of a propanil based herbicide and an effective amount of at least thiobencarb composition to synergistically effect the activity of a imidazolinone herbicide is illustrated by the following examples:

The control of weedy forms of rice weeds is illustrated by the following examples:

EXAMPLE 1 NEWPATH (imazethapyr) 2SL 2 lbs/gal of a soluble liquid formulation) was applied at a rate of 1 oz./acre, a propanil-based herbicide (RICESHOT 4EC (3',4" dichloropropanilide) which is made of 48% propanil active ingredient and 52% inactive ingredients (solvent, emulsifier and adjuvants)), was applied at a rate of 2.25 quart per acre with non-ionic surfactant at a rate of 0.25% v/v. The weedy forms of rice control at 16 days after application (DAA) was observed to be 42.5% with an expected weedy forms of rice control of 7.5% based on Colby's formula (FIG. 1). At 32 days after application, weedy forms of rice control was observed to be 65.2% with an expected weedy forms of rice control of 46.8%. In this combination, synergy was observed because the observed weedy forms of rice control was greater than the expected control. As shown in FIG. 1, this demonstrates the synergistic effect on weedy forms of rice control by adding an EC formulation of propanil to NEWPATH (imazethapyr) 2SL.

Figure 2:
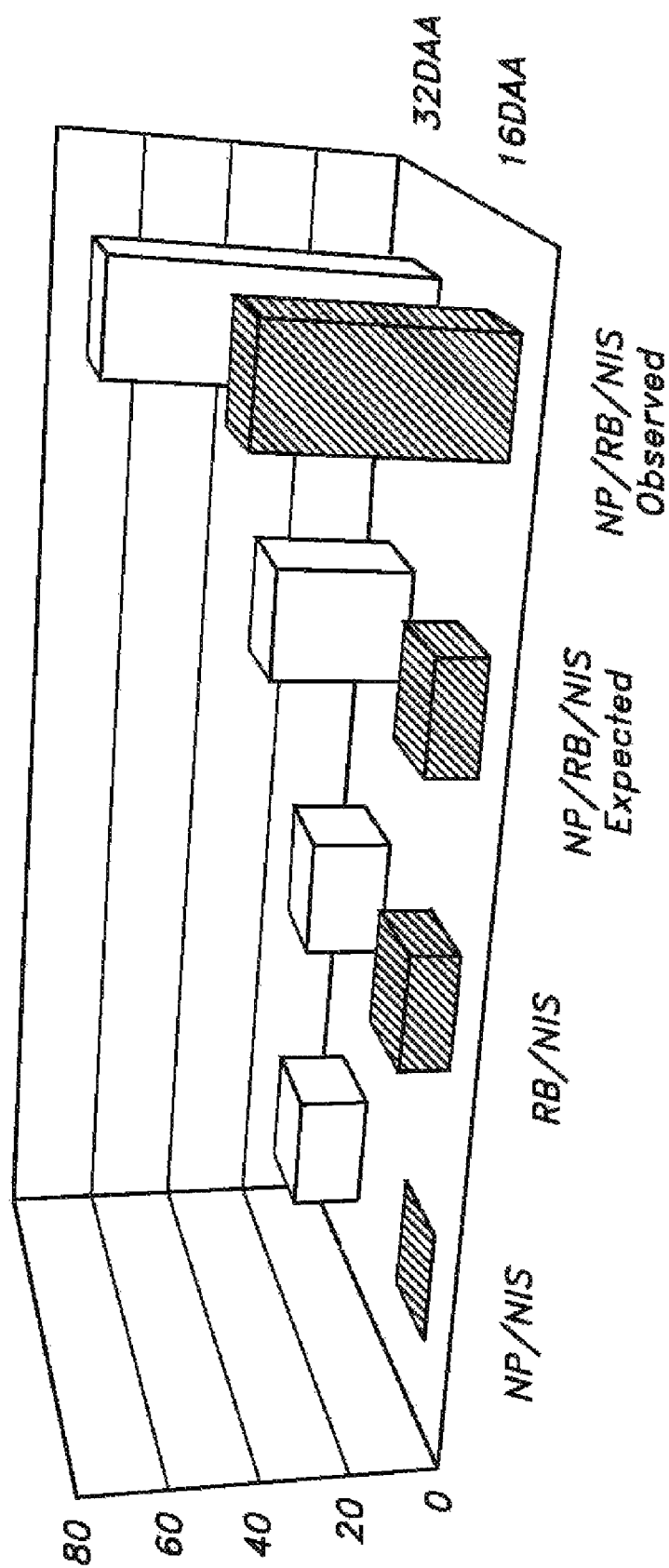
FIG. 2 shows expected versus observed Red Rice control (%) with NEWPATH (1 oz./A.) and RICEBEAUX (3 qt./A.) with NIS (0.25% v/v) at 16 and 32 DDA. Expected values are based on Colby Method (Weeds 15:20-22); Legend: Legend: NP: NEWPATH, NIS: Non-ionic Surfactant and, RB: RICEBEAUX.

EXAMPLE 2 NEWPATH (imazethapyr) 2SL was applied at a rate of 1 oz./acre, a propanil-based herbicide (RICEBEAUX 6EC (3',4" dichloropropanilide and thiobencarb) which is made of 35% propanil active ingredient, 31% thiobencarb active ingredient and 34% inactive ingredients (solvent, emulsifier and adjuvants)) was applied at a rate of 3 quart per acre with non-ionic surfactant at a rate of 0.25% v/v. EC means an emulsifiable concentrate. The weedy forms of rice control at 16 days after application (DAA) was observed to be 53.3% with an expected weedy forms of rice control of 11.7% based on Colby's formula (FIG. 2). At 32 days after application, weedy forms of rice control was observed to be 73.7% with an expected weedy forms of rice control of 32.2%. In this combination, synergy was observed because the observed weedy forms of rice control was greater than the expected control. This demonstrates the synergistic effect on weedy forms of rice control by adding an EC formulation of propanil and thiobencarb to NEWPATH (imazethapyr) 2 SL.

Figure 3:
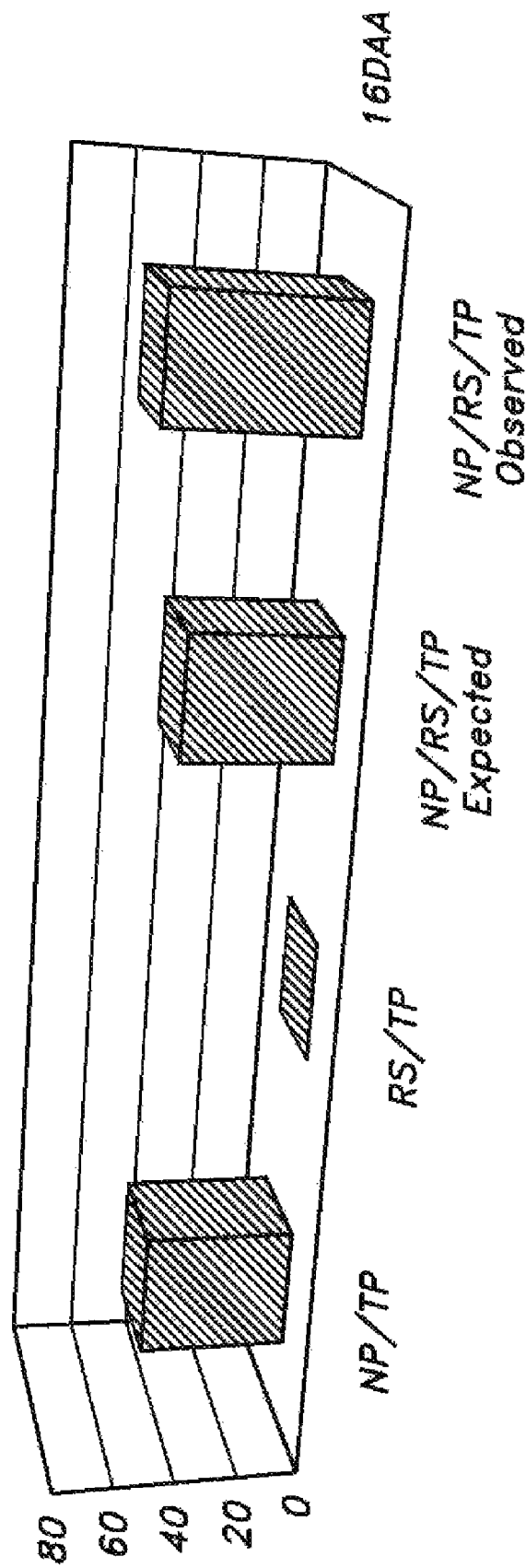
FIG. 3 shows expected versus observed Red Rice control (%) with NEWPATH (1 oz./A.) and RICESHOT (2.25 qt./A.) with TRIPLE PLAY (12.8 oz./A.) at 16 DAA. Expected values are based on Colby Method (Weeds 15:20-22). Legend: NP: NEWPATH, TP: TRIPLE PLAY, and RS: RICESHOT.

EXAMPLE 3 NEWPATH (imazethapyr) 2SL was applied at a rate of 1 oz./acre, a propanil-based herbicide (RICESHOT 4EC (3',4" dichloropropanilide) which is made of 48% propanil active ingredient and 52% inactive ingredients (solvent, emulsifier and adjuvants)), was applied at a rate of 2.25 quart per acre with TRIPLE PLAY (Agxplore Int'l) surfactant at a rate of 12.8 oz. per acre. The weedy forms of rice control at 16 days after application (DAA) was observed to be 60.8% with an expected weedy forms of rice control of 48.3% based on Colby's formula (FIG. 3). In this combination, synergy was observed because the observed weedy forms of rice control was greater than the expected control. This demonstrates the synergistic effect on weedy forms of rice control by adding an EC formulation of propanil to NEWPATH (imazethapyr) 2SL.

Figure 4:
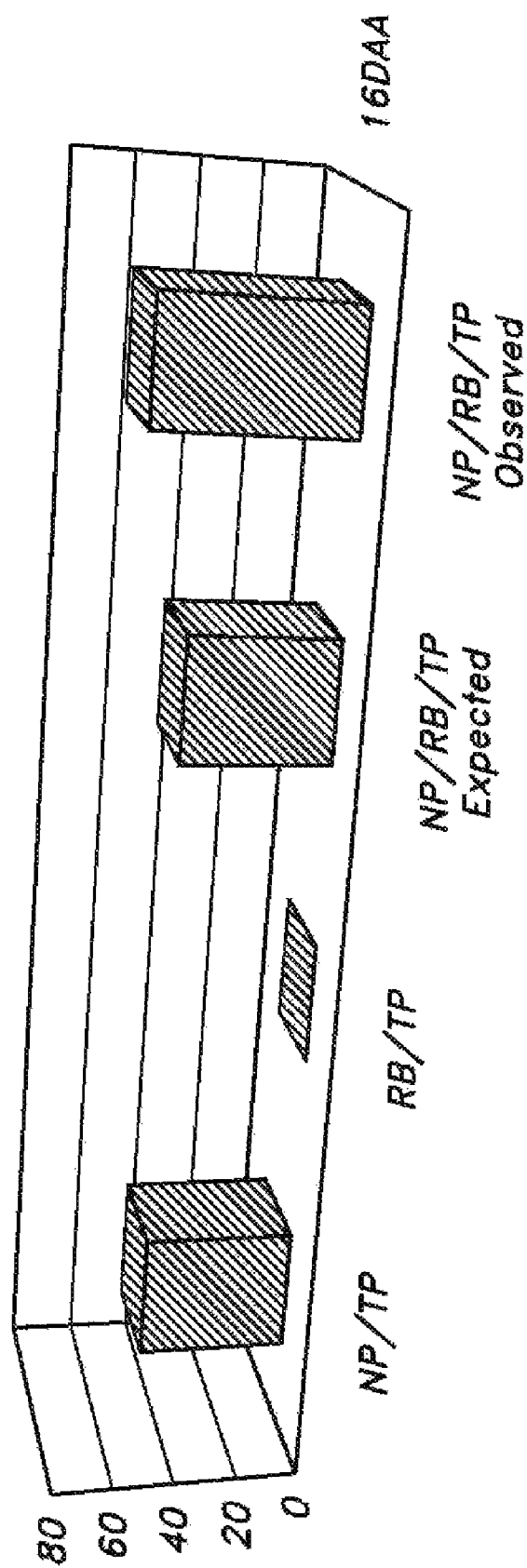
FIG. 4 shows expected versus observed Red Rice control (%) with NEWPATH (1 oz./A.) and RICEBEAUX (3 qt./A.) with TRIPLE PLAY (12.8 oz./A.) at 16 DAA. Legend: NP: NEWPATH, TP: TRIPLE PLAY, and RB: RICEBEAUX.

EXAMPLE 4 NEWPATH (imazethapyr) 2SL was applied at a rate of 1 oz./acre, a propanil-based herbicide (RICEBEAUX 6EC (3',4" dichloropropanilide and thiobencarb) which is made of 35% propanil active ingredient, 31% thiobencarb active ingredient and 34% inactive ingredients (solvent, emulsifier and adjuvants)), was applied at a rate of 3 quart per acre with TRIPLE PLAY (Agxplore Int'l) surfactant at a rate of 12.8 oz. per acre. The weedy forms of rice control at 16 days after application (DAA) was observed to be 64.2% with an expected weedy forms of rice control of 48.3% based on Colby's formula (FIG. 4). In this combination, synergy was observed because the observed weedy forms of rice control was greater than the expected control. This demonstrates the synergistic effect on weedy forms of rice control by adding an EC formulation of propanil with thiobencarb to NEWPATH (imazethapyr) 2SL.

Figure 5:
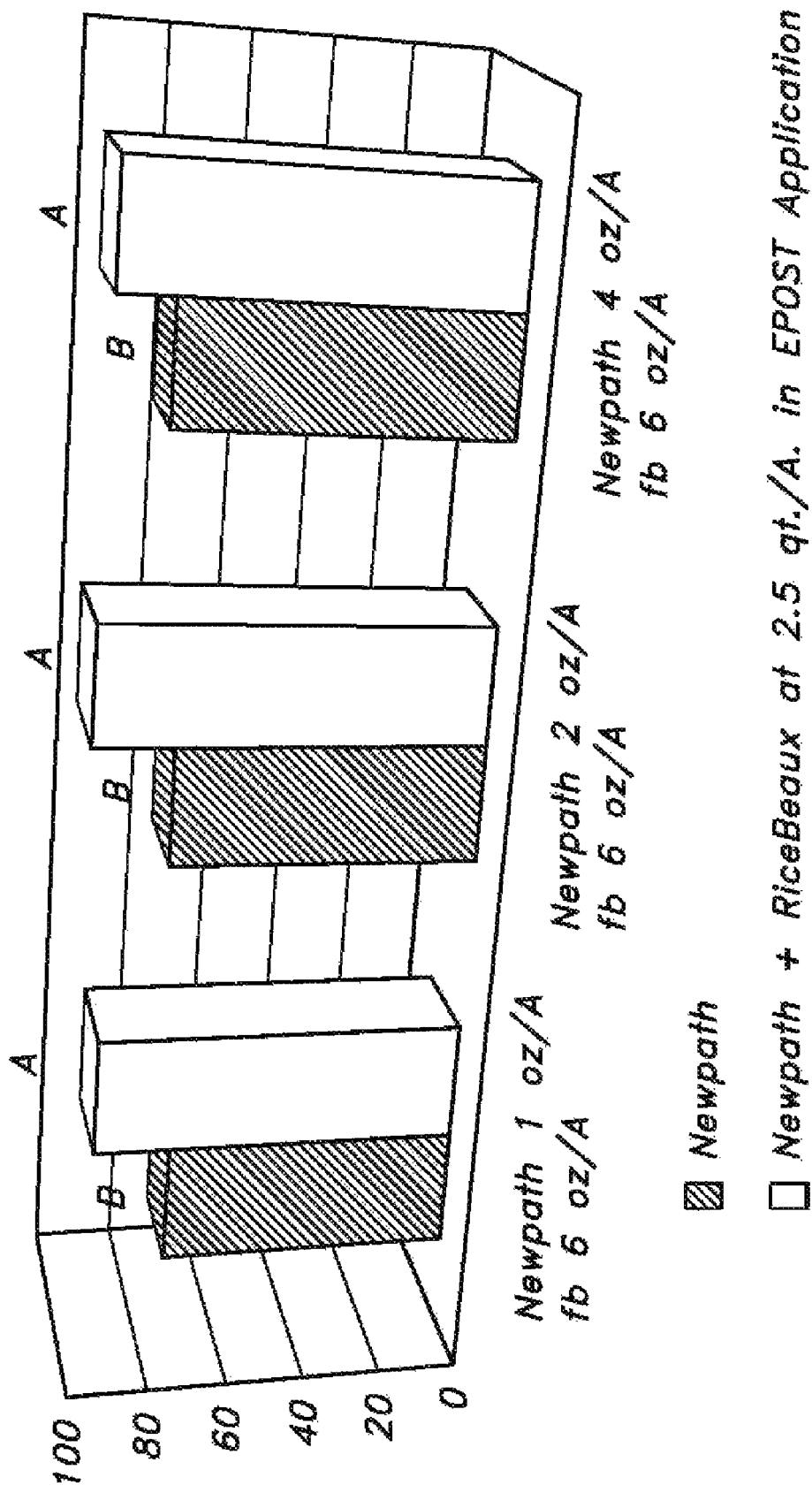

EXAMPLE 5 NEWPATH (imazethapyr) 2SL was applied as the first of two applications (early postemergence) at a rate of 1, 2 and 4 oz./acre with a crop oil concentrate alone and with a propanil-based herbicide (RICEBEAUX 6 EC (3',4" dichloropropanilide and thiobencarb) which is made of 35% propanil active ingredient, 31% thiobencarb active ingredient and 34% inactive ingredients (solvent, emulsifier and adjuvants)), applied at a rate of 2.5 quart per acre. The second application (late postemergence) for all treatments was NEW- PATH (imazethapyr) 2SL applied at 6 oz./acre with crop oil concentrate. Weedy forms of rice control at 22 days after the early postemergence application and 9 days after the late postemergence application was observed to be significantly improved by the addition of RICEBEAUX to all rates of NEWPATH (imazethapyr) 2SL (FIG. 5). In these combinations, synergy was observed because the weedy forms of rice control was statistically greater at all rates of NEWPATH (imazethapyr) 2SL tank-mixed with RICEBEAUX when compared with NEWPATH (imazethapyr) 2SL applied alone. This demonstrates the synergistic effect on weedy forms of rice control by adding an EC formulation of propanil with thiobencarb to NEWPATH (imazethapyr) 2SL. Field trial data is shown in TABLE 1.

Figure 6:
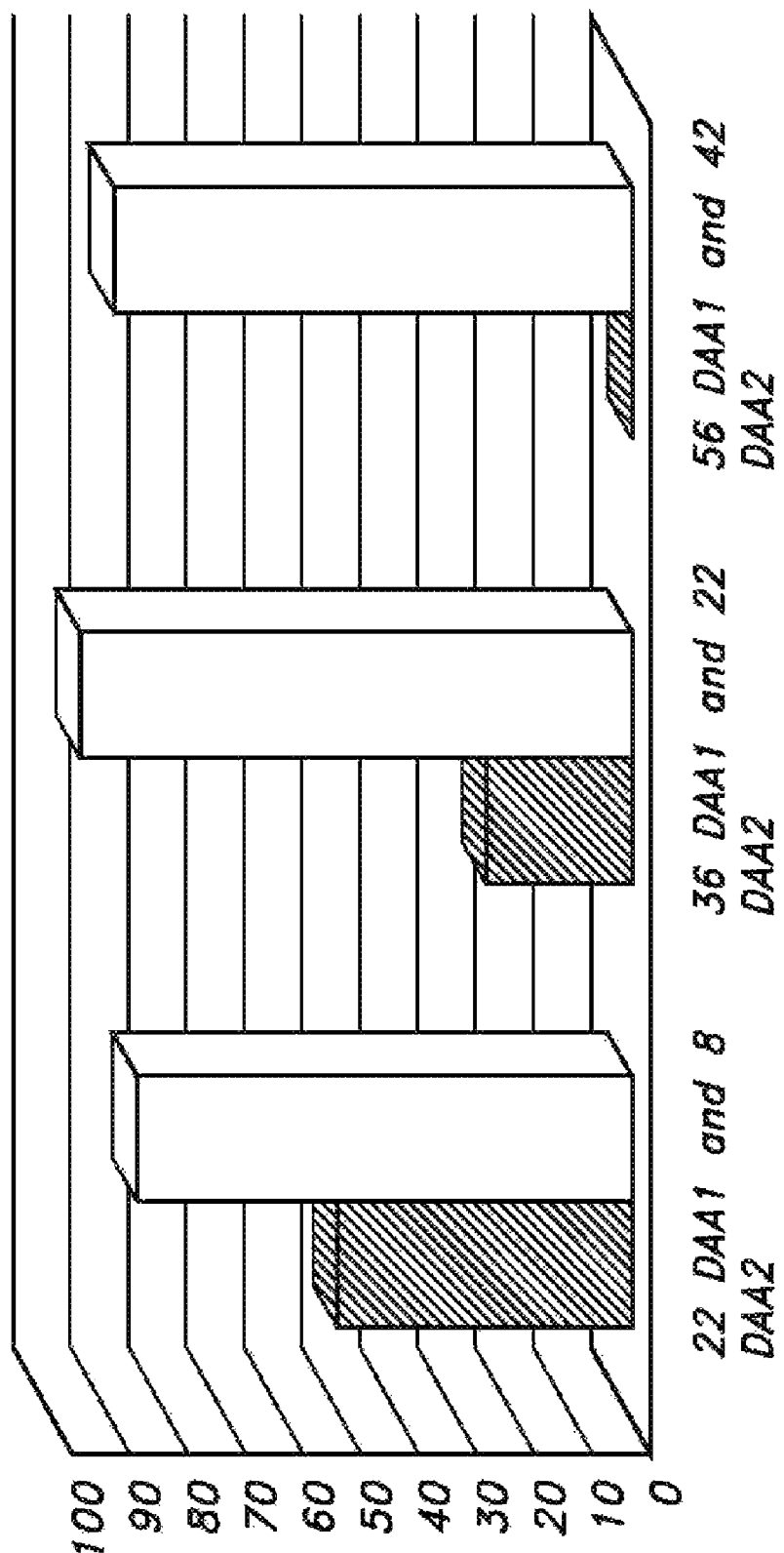
FIG. 6 shows Expected versus observed Red Rice control (%) with Sequential Applications of NEWPATH (1 oz./A.)+ RICEBEAUX (2.5 qt./A.) Expected values are based on Colby Method (Weeds 15:20-22). Legend: DAA1: Days After Application 1, and DAA2: Days After Application 2.
Figure 7:
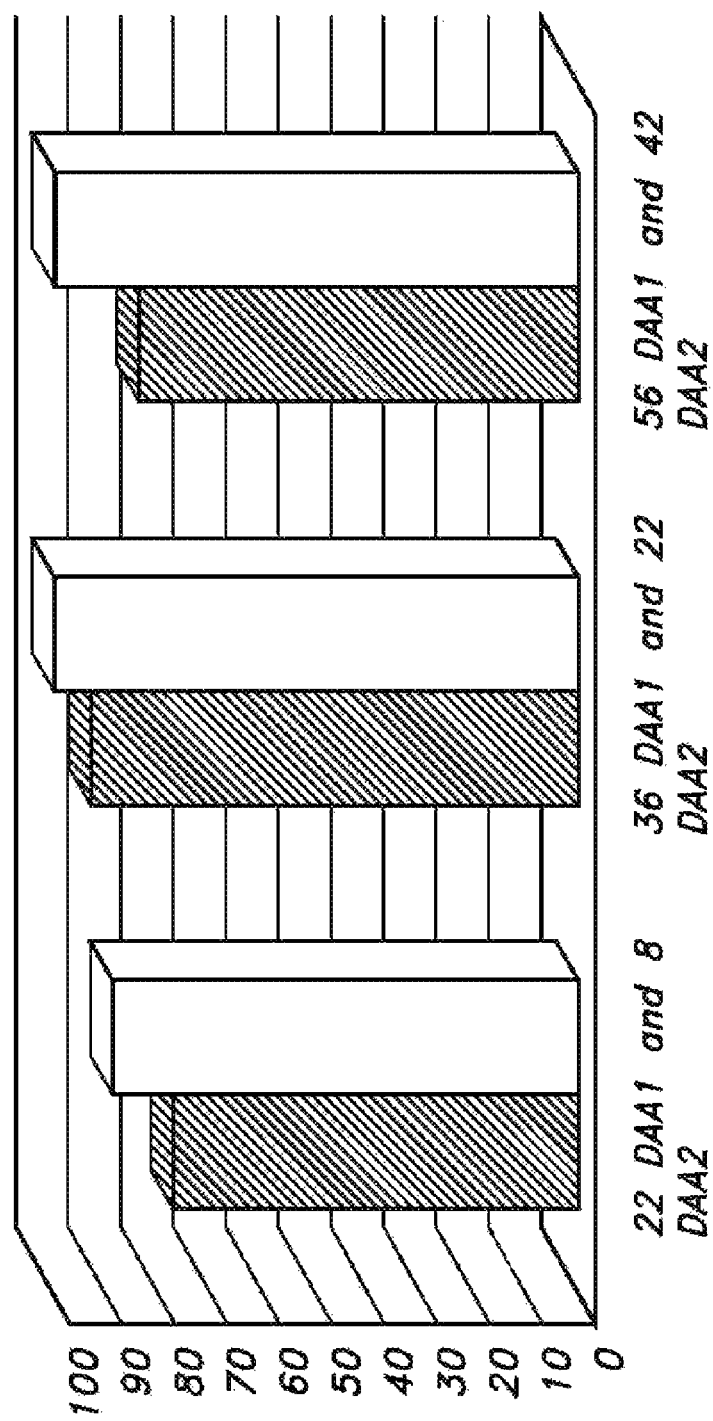
FIG. 7 shows Expected versus observed Red Rice control (%) with Sequential Applications of NEWPATH (2 oz./A.)+ RICEBEAUX (2.5 qt./A.) Expected values are based on Colby Method (Weeds 15:20-22). Expected values are based on Colby Method (Weeds 15:20-22). Legend: DAA1: Days After Application 1, and DAA2: Days After Application 2.
Figure 8:
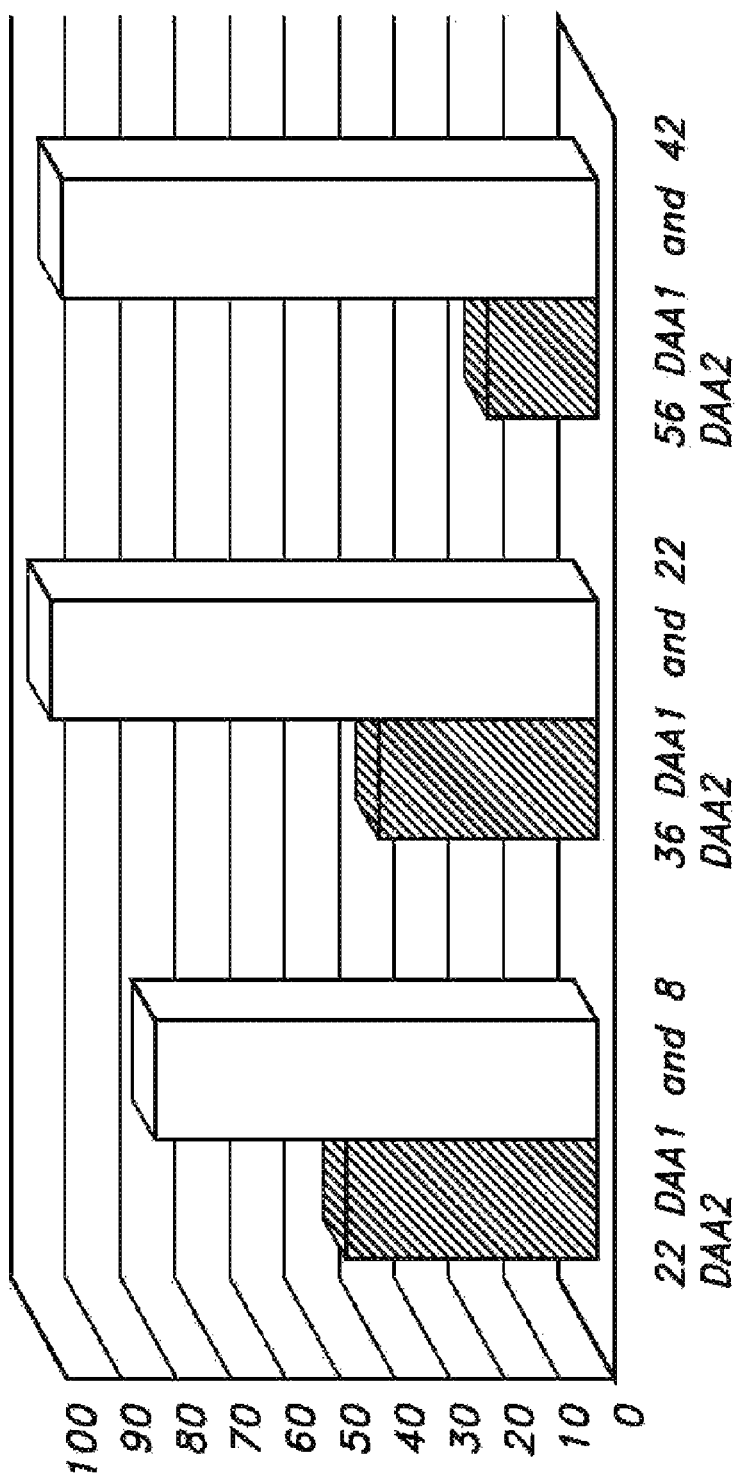
FIG. 8 shows Expected versus observed Red Rice control (%) with Sequential Applications of NEWPATH (4 oz./A.)+ RICEBEAUX (2.5 qt./A.). Expected values are based on Colby Method (Weeds 15:20-22). Legend: DAA1: Days After Application 1, and DAA2: Days After Application 2.

(imazethapyr) 2SL applied at 1, 2 and 4 oz./acre with crop oil concentrate alone and with a propanil-based herbicide (RICEBEAUX 6 EC (3',4" dichloropropanilide and thiobencarb) which is made of 35% propanil active ingredient, 31% thiobencarb active ingredient and 34% inactive ingredients (solvent, emulsifier and adjuvants)), applied at a rate of 2.5 quart per acre. Weedy forms of rice control was evaluated at 22 days after the early postemergence application and 8 days after the late postemergence application, 36 days after the early postemergence application and 22 days after the late postemergence application, and 56 days after the early postemergence application and 42 days after the late postemergence application (FIGS. 6-8). Weedy forms of rice control with all rates of NEWPATH (imazethapyr) 2SL (1, 2, and 4

TABLE 1

| Trt No | Treatment Name | Rate | Rate Unit | Growth Stage | W Weed ORYSA 19 May 2010 % | W Weed ORYSA 26 May 2010 % | W Weed ORYSA 7 Jun. 2010 % | W Weed ORYSA 21 Jun. 2010 % |
|---|---|---|---|---|---|---|---|---|
| 1 | Newpath | 1 | FL OZ/A | EPOST | 33 b | 74 b | 63 b | 65 c |
|   | Agridex | 1 | % V/V | EPOST | | | | |
|   | Newpath | 6 | FL OZ/A | LPOST | | | | |
|   | Agridex | 1 | % V/V | LPOST | | | | |
| 2 | Newpath | 2 | FL OZ/A | EPOST | 35 b | 78 b | 70 b | 76 bc |
|   | Agridex | 1 | % V/V | EPOST | | | | |
|   | Newpath | 6 | FL OZ/A | LPOST | | | | |
|   | Agridex | 1 | % V/V | LPOST | | | | |
| 3 | Newpath | 4 | FL OZ/A | EPOST | 35 b | 83 b | 88 a | 85 ab |
|   | Agridex | 1 | % V/V | EPOST | | | | |
|   | Newpath | 6 | FL OZ/A | LPOST | | | | |
|   | Agridex | 1 | % V/V | LPOST | | | | |
| 4 | Newpath | 1 | FL OZ/A | EPOST | 40 b | 93 a | 96 a | 66 c |
|   | RiceBeaux | 2.5 | QT/A | EPOST | | | | |
|   | Agridex | 1 | % V/V | EPOST | | | | |
|   | Newpath | 6 | FL OZ/A | LPOST | | | | |
|   | Agridex | 1 | % V/V | LPOST | | | | |
| 5 | Newpath | 2 | FL OZ/A | EPOST | 76 a | 98 a | 98 a | 94 a |
|   | RiceBeaux | 2.5 | QT/A | EPOST | | | | |
|   | Agridex | 1 | % V/V | EPOST | | | | |
|   | Newpath | 6 | FL OZ/A | LPOST | | | | |
|   | Agridex | 1 | % V/V | LPOST | | | | |
| 6 | Newpath | 4 | FL OZ/A | EPOST | 78 a | 97 a | 96 a | 93 a |
|   | RiceBeaux | 2.5 | QT/A | EPOST | | | | |
|   | Agridex | 1 | % V/V | EPOST | | | | |
|   | Newpath | 6 | FL OZ/A | LPOST | | | | |
|   | Agridex | 1 | % V/V | LPOST | | | | |
| 7 | RiceBeaux | 2.5 | QT/A | EPOST | 18 c | 73 b | 66 b | 23 d |
|   | Newpath | 6 | FL OZ/A | LPOST | | | | |
|   | Agridex | 1 | % V/V | LPOST | | | | |
| 8 | Nontreated | | | | 0 d | 0 c | 0 c | 0 c |
| LSD (P = .05) | | | | | 13.9 | 10.2 | 11.2 | 16.6 |
| Standard Deviation | | | | | 9.5 | 6.9 | 7.6 | 11.3 |
| CV | | | | | 24.12 | 9.31 | 10.52 | 17.97 |
| Grand Mean | | | | | 39.22 | 74.34 | 72.06 | 62.75 |
| Bartlett's X2 | | | | | 7.613 | 10.863 | 11.099 | 14.736 |
| P(Bartlett's X2) | | | | | 0.268 | 0.054 | 0.025* | 0.0222 |
| Replicate F | | | | | 0.614 | 2.371 | 0.959 | 3.688 |
| Replicate Prob(F) | | | | | 0.6134 | 0.0994 | 0.4304 | 0.0281 |
| Treatment F | | | | | 31.473 | 84.049 | 73.437 | 36.590 |
| Treatment Prob(F) | | | | | 0.0001 | 0.0001 | 0.0001 | 0.0001 |

EXAMPLE 6: NEWPATH (imazethapyr) 2SL was applied as the first of two applications (early postemergence) at a rate of 1, 2 and 4 oz./acre with a crop oil concentrate alone and with a propanil-based herbicide (RICEBEAUX 6 EC (3',4" dichloropropanilide and thiobencarb) which is made of 35% propanil active ingredient, 31% thiobencarb active ingredient and 34% inactive ingredients (solvent, emulsifier and adjuvants)), applied at a rate of 2.5 quart per acre. The second application (late postemergence) was NEWPATH (imazethapyr) 2SL applied at 6 oz./A. The combined with RICEBEAUX at 2.5 qt./A. at all evaluation timings was observed to be greater than expected based on Colby's formula. In these combinations, synergy was observed because the observed weedy forms of rice control was greater than the expected control. This demonstrates the synergistic effect on weedy forms of rice control of adding an EC formulation of propanil with thiobencarb to NEWPATH (imazethapyr) 2SL. Field trial data is shown in TABLE 2.

TABLE 2

| Trt No. | Treatment Name | Rate | Rate Unit | Growth Stage | Pest Type: W Weed<br>Pest Code: ORYSA<br>Rating Date: 3 Jun. 2010<br>Rating Unit: % | Pest Type: W Weed<br>Pest Code: ORYSA<br>Rating Date: 17 Jun. 2010<br>Rating Unit: % | Pest Type: W Weed<br>Pest Code: ORYSA<br>Rating Date: 7 Aug. 2010<br>Rating Unit: % |
|---|---|---|---|---|---|---|---|
| 1 | Newpath | 1 | FL OZ/A | 1-2 lf | 3 g | 0 d | 3 i |
| 2 | Newpath | 2 | FL OZ/A | 1-2 lf | 15 efg | 0 d | 3 i |
| 3 | Newpath | 4 | FL OZ/A | 1-2 lf | 16 efg | 8 cd | 10 h |
| 4 | RiceBeaux | 2.5 | QT/A | 1-2 lf | 15 efg | 0 d | 0 i |
| 5 | Newpath | 1 | FL OZ/A | 1-2 lf | 33 b-f | 18 bcd | 15 g |
|   | RiceBeaux | 2.5 | QT/A | 1-2 lf | | | |
| 6 | Newpath | 2 | FL OZ/A | 1-2 lf | 48 bc | 35 bc | 25 f |
|   | RiceBeaux | 2.5 | QT/A | 1-2 lf | | | |
| 7 | Newpath | 4 | FL OZ/A | 1-2 lf | 78 a | 93 a | 91 b |
|   | RiceBeaux | 2.5 | QT/A | 1-2 lf | | | |
| 8 | Newpath | 1 | FL OZ/A | 4-6 lf | 20 d-g | 3 d | 0 i |
| 9 | Newpath | 2 | FL OZ/A | 4-6 lf | 10 fg | 0 d | 0 i |
| 10 | Newpath | 4 | FL OZ/A | 4-6 lf | 35 b-c | 5 d | 0 i |
| 11 | RiceBeaux | 2.5 | QT/A | 4-6 lf | 15 efg | 0 d | 0 i |
| 12 | Newpath | 1 | FL OZ/A | 4-6 lf | 28 b-f | 25 bcd | 20 fg |
|   | RiceBeaux | 2.5 | QT/A | 4-6 lf | | | |
| 13 | Newpath | 2 | FL OZ/A | 4-6 lf | 40 bcd | 43 b | 30 e |
|   | RiceBeaux | 2.5 | QT/A | 4-6 lf | | | |
| 14 | Newpath | 4 | FL OZ/A | 4-6 lf | 50 b | 83 a | 63 d |
|   | RiceBeaux | 2.5 | QT/A | 4-6 lf | | | |
| 15 | Newpath | 1 | FL OZ/A | 1-2 lf | 35 b-c | 0 d | 0 i |
|   | Newpath | 1 | FL OZ/A | 4-6 lf | | | |
| 16 | Newpath | 2 | FL OZ/A | 1-2 lf | 28 b-f | 20 bcd | 20 fg |
|   | Newpath | 2 | FL OZ/A | 4-6 lf | | | |
| 17 | Newpath | 4 | FL OZ/A | 1-2 lf | 70 a | 91 a | 84 c |
|   | Newpath | 4 | FL OZ/A | 4-6 lf | | | |
| 18 | RiceBeaux | 2.5 | QT/A | 1-2 lf | 25 c-g | 25 bcd | 0 i |
|   | RiceBeaux | 2.5 | QT/A | 4-6 lf | | | |
| 19 | Newpath | 1 | FL OZ/A | 1-2 lf | 86 a | 96 a | 90 b |
|   | RiceBeaux | 2.5 | QT/A | 1-2 lf | | | |
|   | Newpath | 1 | FL OZ/A | 4-6 lf | | | |
|   | RiceBeaux | 2.5 | QT/A | 4-6 lf | | | |
| 20 | Newpath | 2 | FL OZ/A | 1-2 lf | 81 a | 100 a | 98 a |
|   | RiceBeaux | 2.5 | QT/A | 1-2 lf | | | |
|   | Newpath | 2 | FL OZ/A | 4-6 lf | | | |
|   | RiceBeaux | 2.5 | QT/A | 4-6 lf | | | |
| 21 | Newpath | 4 | FL OZ/A | 1-2 lf | 89 a | 100 a | 100 a |
|   | RiceBeaux | 2.5 | QT/A | 1-2 lf | | | |
|   | Newpath | 4 | FL OZ/A | 4-6 lf | | | |
|   | RiceBeaux | 2.5 | QT/A | 4-6 lf | | | |
| LSD (P = .05) | | | | | 14.6 | 19.3 | 4.9 |
| Standard Deviation | | | | | 10.3 | 13.7 | 3.5 |
| CV | | | | | 26.46 | 38.64 | 11.25 |
| Grand Mean | | | | | 38.92 | 35.36 | 30.95 |
| Bartlett's X2 | | | | | 17.345 | 45.535 | 8.762 |
| P(Bartlett's X2) | | | | | 0.567 | 0.001* | 0.46 |
| Freidman's X2 | | | | | 67.45 | 63.052 | 72.903 |
| P(Freidman's X2) | | | | | 0.001 | 0.001 | 0.001 |

Means followed by same letter do not significantly differ (P = .05, Student-Newman-Keuls)
Mean comparisons performed only when AOV Treatment P(F) is significant at mean comparison OSL EXAMPLE 7 NEWPATH (imazethapyr) 2SL is applied at a rate of 1 oz per acre, BOLERO 8EC (Kumiai Chemical Industry) which is made of S-[(4-chlorophenyl)methyl]diethylcarbamothioate per gallon at a rate of 2.25 pt/acre and a NIS (nonionic surfactant) 1 L at a rate of 0.25 percent v/v. The weedy forms of rice control at 16-DAA was 67.5 with an expected red-rice control based on Colby's formula of 0. In this combination synergy was observed because the observed control versus the expected values is different.

EXAMPLE 8 NEWPATH (imazethapyr) 2SL is applied at a rate of 1 oz per acre, BOLERO 8EC (Kumiai Chemical Industry) which is made of S-[(4-chlorophenyl)methyl]diethylcarbamothioate per gallon at a rate of 2.25 pt/acre and TRIPLE PLAY (Agxplore Int'l) 1 L at a rate of 12.8 oz/acre. TRIPLE PLAY (Agxplore Int'l) is a blend of deposition agents, nonionic surfactants, and activators that enhance the effectiveness of agricultural sprays. The weedy forms of rice control at 16-DAA was 64.2 with an expected red-rice control based on Colby's formula of 57.3. In this combination synergy was observed because the observed control versus the expected values is different.

EXAMPLE 9 NEWPATH (imazethapyr) 2SL is applied at a rate of 2 oz per acre, RICESHOT 4EC (3',4" Dichloropropanilide) which is made of 43.50% active ingredient and 56.50% inactive ingredient (solvent and an emulsifier) at a rate of 2.25 qt/a and NIS (nonionic surfactant) 1 L at a rate of 0.25 percent v/v. The weedy forms of rice control at 16-DAA was 59.2 with an expected red-rice control based on Colby's formula of 21.4. In this combination synergy was observed because the observed control versus the expected values is different.

EXAMPLE 10 NEWPATH (imazethapyr) 2SL is applied at a rate of 2 oz per acre, RICESHOT 4EC (3',4" Dichloropropanilide) which is made of 43.50% active ingredient and 56.50% inactive ingredient (solvent and an emulsifier) at a rate of 2.25 qt/a and TRIPLE PLAY (Agxplore Int'l) 1 L at a rate of 12.8 oz/acre. TRIPLE PLAY (Agxplore Int'l) is a blend of deposition agents, nonionic surfactants, and activators that enhance the effectiveness of agricultural sprays. The weedy forms of rice control at 16-DAA was 70.8 with an expected red-rice control based on Colby's formula of 51.7. In this combination synergy was observed because the observed control versus the expected values is different.

EXAMPLE 11 NEWPATH (imazethapyr) 2SL is applied at a rate of 2 oz per acre, RICEBEAUX 6EC which is made of 35% (3',4" Dichloropropanilide) and 31% thiobencarb as the active ingredient and 33% inactive ingredient (solvent and an emulsifier) at a rate of 3.0 qt/a and a NIS (nonionic surfactant) 1 L at a rate of 0.25 percent v/v The weedy forms of rice control at 16-DAA was 66.7 with an expected red-rice control based on Colby's formula of 51.7. In this combination synergy was observed because the observed control versus the expected values is different.

EXAMPLE 12 NEWPATH (imazethapyr) 2SL is applied at a rate of 2 oz per acre, RICEBEAUX 6EC which is made of 35% (3',4" Dichloropropanilide) and 31% thiobencarb as the active ingredient and 33% inactive ingredient (solvent and an emulsifier) at a rate of 3.0 qt/a and TRIPLE PLAY (Agxplore Int'l) 1 L at a rate of 12.8 oz/acre. TRIPLE PLAY (Agxplore Int'l) is a blend of deposition agents, nonionic surfactants, and activators that enhance the effectiveness of agricultural sprays. The weedy forms of rice control at 16-DAA was 62.5 with an expected red-rice control based on Colby's formula of 15.0. In this combination synergy was observed because the observed control versus the expected values is different.

TABLE 3

| Trt No. | Treatment Name | Form Conc | Form Type | Rate | Rate Unit | Weedy form of rice control 16-daa | Expected Weedy form of rice Control based on Colby's Formula |
|---|---|---|---|---|---|---|---|
| 1 | Newpath | 2 | SL | 1 | oz/a | 42.5 | 7.5 |
|  | Riceshot | 4 | EC | 2.25 | qt/a |  |  |
|  | NIS | 1 | L | 0.25 | % v/v |  |  |
| 2 | Newpath | 2 | SL | 1 | oz/a | 60.8 | 48.3 |
|  | Riceshot | 4 | EC | 2.25 | qt/a |  |  |
|  | Triple Play | 1 | L | 12.8 | oz/a |  |  |
| 3 | Newpath | 2 | SL | 1 | oz/a | 53.3 | 11.7 |
|  | Ricebeaux | 6 | EC | 3 | qt/a |  |  |
|  | NIS | 1 | L | 0.25 | % v/v |  |  |
| 4 | Newpath | 2 | SL | 1 | oz/a | 64.2 | 48.3 |
|  | Ricebeaux | 6 | EC | 3 | qt/a |  |  |
|  | Triple Play | 1 | L | 12.8 | oz/a |  |  |
| 5 | Newpath | 2 | SL | 1 | oz/a | 67.5 | 0 |
|  | Bolero | 8 | EC | 2.25 | pt/a |  |  |
|  | NIS | 1 | L | 0.25 | % v/v |  |  |
| 6 | Newpath | 2 | SL | 1 | oz/a | 64.2 | 57.3475 |
|  | Bolero | 8 | EC | 2.25 | pt/a |  |  |
|  | Triple Play | 1 | L | 12.8 | oz/a |  |  |
| 7 | Newpath | 2 | SL | 2 | oz/a | 59.2 | 21.375 |
|  | Riceshot | 4 | EC | 2.25 | qt/a |  |  |
|  | NIS | 1 | L | 0.25 | % v/v |  |  |
| 8 | Newpath | 2 | SL | 2 | oz/a | 70.8 | 51.7 |
|  | Riceshot | 4 | EC | 2.25 | qt/a |  |  |
|  | Triple Play | 1 | L | 12.8 | oz/a |  |  |
| 9 | Newpath | 2 | SL | 2 | oz/a | 68.3 | 24.945 |
|  | Ricebeaux | 6 | EC | 3 | qt/a |  |  |
|  | NIS | 1 | L | 0.25 | % v/v |  |  |
| 10 | Newpath | 2 | SL | 2 | oz/a | 66.7 | 51.7 |
|  | Ricebeaux | 6 | EC | 3 | qt/a |  |  |
|  | Triple Play | 1 | L | 12.8 | oz/a |  |  |
| 11 | Newpath | 2 | SL | 2 | oz/a | 62.5 | 15 |
|  | Bolero | 8 | EC | 2.25 | pt/a |  |  |
|  | NIS | 1 | L | 0.25 | % v/v |  |  |
| LSD (P = .05) |  |  |  |  |  | 16.07 |  |
| Standard Deviation |  |  |  |  |  | 14.06 |  |
| CV |  |  |  |  |  | 37.27 |  |
| Grand Mean |  |  |  |  |  | 37.73 |  |
| Bartlett's X2 |  |  |  |  |  | 71.679 |  |
| P(Bartlett's X2) |  |  |  |  |  |  | 0.001* |
| Replicate F |  |  |  |  |  | 2.779 |  |
| Replicate Prob(F) |  |  |  |  |  |  | 0.0195 |
| Treatment F |  |  |  |  |  | 21.303 |  |
| Treatment Prob(F) |  |  |  |  |  |  | 0.0001 |

Means followed by same letter do not significantly differ (P = .05, LSD)
Mean comparisons performed only when AOV Treatment P(F) is significant at mean comparison OSL.

TABLE 4

| Treatment Number | Treatment | Formulation Strength | Formulation Type | Rate | Units | Application Timing | Red Rice Control at 16 DAA* | Red Rice Control at 32 DAA* |
|---|---|---|---|---|---|---|---|---|
| 1 | Newpath | 2 | SL | 1 | oz/a | 2-3lfrice | 0 h | 16.8 ij |
|   | NIS | 1 | L | 0.25 | % v/v | 2-3lfrice | | |
| 2 | Newpath | 2 | SL | 1 | oz/a | 2-3lfrice | 17.5 g | 27.8 ij |
|   | COC | 1 | L | 1 | % v/v | 2-3lfrice | | |
| 3 | Newpath | 2 | SL | 1 | oz/a | 2-3lfrice | 48.3 def | 89.2 a-e |
|   | Triple Play | 1 | L | 12.8 | oz/a | 2-3lfrice | | |
| 4 | Newpath | 2 | SL | 2 | oz/a | 2-3lfrice | 15 gh | 71.8 cf |
|   | NIS | 1 | L | 0.25 | % v/v | 2-3lfrice | | |
| 5 | Newpath | 2 | SL | 2 | oz/a | 2-3lfrice | 50 def | 84.3 a-f |
|   | COC | 1 | L | 1 | % v/v | 2-3lfrice | | |
| 6 | Newpath | 2 | SL | 2 | oz/a | 2-3lfrice | 51.7 c-f | 93.2 abc |
|   | Triple Play | 1 | L | 12.8 | oz/a | 2-3lfrice | | |
| 7 | Riceshot | 4 | EC | 2.25 | qt/a | 2-3lfrice | 7.5 gh | 36 hi |
|   | NIS | 1 | L | 0.25 | % v/v | 2-3lfrice | | |
| 8 | Riceshot | 4 | EC | 2.25 | qt/a | 2-3lfrice | 0 h | 27.7 ij |
|   | Triple Play | 1 | L | 12.8 | oz/a | 2-3lfrice | | |
| 9 | Ricebeaux | 6 | EC | 3 | qt/a | 2-3lfrice | 11.7 gh | 18.5 ij |
|   | NIS | 1 | L | 0.25 | % v/v | 2-3lfrice | | |
| 10 | Ricebeaux | 6 | EC | 3 | qt/a | 2-3lfrice | 0 h | 26.3 ij |
|    | Triple Play | 1 | L | 12.8 | oz/a | 2-3lfrice | | |
| 11 | Bolero | 8 | EC | 2.25 | pt/a | 2-3lfrice | 0 h | 31 hij |
|    | NIS | 1 | L | 0.25 | % v/v | 2-3lfrice | | |
| 12 | Bolero | 8 | EC | 2.25 | pt/a | 2-3lfrice | 17.5 g | 30.2 hij |
|    | Triple Play | 1 | L | 12.8 | oz/a | 2-3lfrice | | |
| 13 | Newpath | 2 | SL | 1 | oz/a | 2-3lfrice | 42.5 ef | 65.2 fg |
|    | Riceshot | 4 | EC | 2.25 | qt/a | 2-3lfrice | | |
|    | NIS | 1 | L | 0.25 | % v/v | 2-3lfrice | | |
| 14 | Newpath | 2 | SL | 1 | oz/a | 2-3lfrice | 60.8 a-d | 90.2 a-c |
|    | Riceshot | 4 | EC | 2.25 | qt/a | 2-3lfrice | | |
|    | Triple Play | 1 | L | 12.8 | oz/a | 2-3lfrice | | |
| 15 | Newpath | 2 | SL | 1 | oz/a | 2-3lfrice | 53.3 b-f | 73.7 c-f |
|    | Ricebeaux | 6 | EC | 3 | qt/a | 2-3lfrice | | |
|    | NIS | 1 | L | 0.25 | % v/v | 2-3lfrice | | |
| 16 | Newpath | 2 | SL | 1 | oz/a | 2-3lfrice | 64.2 a-d | 73 def |
|    | Ricebeaux | 6 | EC | 3 | qt/a | 2-3lfrice | | |
|    | Triple Play | 1 | L | 12.8 | oz/a | 2-3lfrice | | |
| 17 | Newpath | 2 | SL | 1 | oz/a | 2-3lfrice | 67.5 abc | 93.5 ab |
|    | Bolero | 8 | EC | 2.25 | pt/a | 2-3lfrice | | |
|    | NIS | 1 | L | 0.25 | % v/v | 2-3lfrice | | |
| 18 | Newpath | 2 | SL | 1 | oz/a | 2-3lfrice | 64.2 a-d | 94 ab |
|    | Bolero | 8 | EC | 2.25 | pt/a | 2-3lfrice | | |
|    | Triple Play | 1 | L | 12.8 | oz/a | 2-3lfrice | | |
| 19 | Newpath | 2 | SL | 2 | oz/a | 2-3lfrice | 59.2 a-d | 80.8 a-f |
|    | Riceshot | 4 | EC | 2.25 | qt/a | 2-3lfrice | | |
|    | NIS | 1 | L | 0.25 | % v/v | 2-3lfrice | | |
| 20 | Newpath | 2 | SL | 2 | oz/a | 2-3lfrice | 70.8 a | 92.3 a-d |
|    | Riceshot | 4 | EC | 2.25 | qt/a | 2-3lfrice | | |
|    | Triple Play | 1 | L | 12.8 | oz/a | 2-3lfrice | | |
| 21 | Newpath | 2 | SL | 2 | oz/a | 2-3lfrice | 68.3 ab | 96.5 a |
|    | Ricebeaux | 6 | EC | 3 | qt/a | 2-3lfrice | | |
|    | NIS | 1 | L | 0.25 | % v/v | 2-3lfrice | | |
| 22 | Newpath | 2 | SL | 2 | oz/a | 2-3lfrice | 66.7 abc | 95.3 ab |
|    | Ricebeaux | 6 | EC | 3 | qt/a | 2-3lfrice | | |
|    | Triple Play | 1 | L | 12.8 | oz/a | 2-3lfrice | | |
| 23 | Newpath | 2 | SL | 2 | oz/a | 2-3lfrice | 62.5 a-d | 96 a |
|    | Bolero | 8 | EC | 2.25 | pt/a | 2-3lfrice | | |
|    | NIS | 1 | L | 0.25 | % v/v | 2-3lfrice | | |
| 24 | Newpath | 2 | SL | 2 | oz/a | 2-3lfrice | 58.3 a-E | 95.7 ab |
|    | Bolero | 8 | EC | 2.25 | pt/a | 2-3lfrice | | |
|    | Triple Play | 1 | L | 12.8 | oz/a | 2-3lfrice | | |
| LSD (P = .05) | | | | | | | 16.07 | 19.81 |
| Standard Deviation | | | | | | | 14.06 | 17.33 |
| CV | | | | | | | 37.27 | 27.54 |
| Grand Mean | | | | | | | 37.73 | 62.92 |
| Bartlett's X2 | | | | | | | 71.679 | 119.439 |
| P(Bartlett's X2) | | | | | | | 0.001* | 0.001* |
| Replicate F | | | | | | | 2.779 | 0.281 |
| Replicate Prob(F) | | | | | | | 0.0195 | 0.9231 |
| Treatment F | | | | | | | 21.303 | 19.124 |
| Treatment Prob(F) | | | | | | | 0.0001 | 0.0001 |

*Means followed by the same letter are not significantly different.

The various embodiments described above are provided by way of illustration only and should not be construed to limit the invention. Those skilled in the art will readily recognize various modifications and changes that may be made to the present invention without following the example embodiments and applications illustrated and described herein, and without departing from the true spirit and scope of the present invention, which is set forth in the following claims.

The invention claimed is:

1. A method to increase the effectiveness of imazethapyr to suppress weedy forms of rice growth used with imidazolinone tolerant rice strains comprising:
    applying imazethapyr to said rice; and
    applying a propanil based herbicide to said rice, wherein said propanil based herbicide includes an herbicidally effective amount of an herbicidally active ingredient including propanil and a synergistically effective amount of an herbicidally inactive ingredient, to synergistically affect the activity of imazethapyr by increasing the effectiveness of imazethapyr used with said rice to suppress weedy forms of rice growth.

2. The method of claim 1 wherein said herbicidally inactive ingredient is an effective amount of a non-ionic surfactant to synergistically affect the activity of imazethapyr.

3. The method of claim 1 wherein said herbicidally inactive ingredient is an effective amount of an adjuvant to synergistically affect the activity of imazethapyr.

4. The method of claim 1 wherein said herbicidally inactive ingredient is an effective amount of a surfactant to synergistically affect the activity of imazethapyr.

5. The method of claim 1 wherein said herbicidally inactive ingredient in an effective amount of a crop-oil concentrate to synergistically affect the activity of imazethapyr.

6. The method of claim 1 further comprising applying a herbicidally effective amount of thiobencarb.

7. The method of claim 1 further comprising applying an herbicidally effective amount of quinclorac.

8. A method to increase the effectiveness of imazethapyr to suppress weedy forms of rice growth used with imidazolinone tolerant rice strains comprising:
    applying an imidazolinone herbicide to said rice; and
    applying a thiobencarb based herbicide to said rice, wherein said thiobencarb based herbicide includes a herbicidally effective amount of an herbicidally active ingredient including thiobencarb and a synergistically effective amount of an herbicidally inactive ingredient, to synergistically affect the activity of imazethapyr by increasing the effectiveness of an imidazolinone herbicide used with said rice to suppress weedy forms of rice growth.

9. The method of claim 8 wherein said herbicidally inactive ingredient is an effective amount of a non-ionic surfactant to synergistically affect the activity of imazethapyr.

10. The method of claim 8 wherein said herbicidally inactive ingredient is an effective amount of an adjuvant to synergistically affect the activity of imazethapyr.

11. The method of claim 8 wherein said herbicidally inactive ingredient is an effective amount of a surfactant to synergistically affect the activity of imazethapyr.

12. The method of claim 8 wherein said herbicidally inactive ingredient in an effective amount of a crop-oil concentrate to synergistically affect the activity of imazethapyr.

13. The method of claim 8 further comprising applying an herbicidally effective amount of propanil.

14. The method of claim 8 further comprising applying an herbicidally effective amount of quinclorac.

* * * * *